(12) United States Patent
Hoppmann et al.

(10) Patent No.: US 9,801,611 B2
(45) Date of Patent: Oct. 31, 2017

(54) ULTRASOUND BARRIER DEVICES AND METHODS RELATED THERETO

(71) Applicants: Richard A. Hoppmann, Columbia, SC (US); Debra Krotish, Blythewood, SC (US); Shaun Riffle, Lexington, SC (US)

(72) Inventors: Richard A. Hoppmann, Columbia, SC (US); Debra Krotish, Blythewood, SC (US); Shaun Riffle, Lexington, SC (US)

(73) Assignee: University of South Carolina, Columbia, SC (US)

( * ) Notice: Subject to any disclaimer, the term of this patent is extended or adjusted under 35 U.S.C. 154(b) by 566 days.

(21) Appl. No.: 14/079,933

(22) Filed: Nov. 14, 2013

(65) Prior Publication Data

US 2014/0135629 A1    May 15, 2014

Related U.S. Application Data

(60) Provisional application No. 61/726,929, filed on Nov. 15, 2012.

(51) Int. Cl.
*A61B 90/40* (2016.01)
*A61B 8/00* (2006.01)
*A61B 8/08* (2006.01)
*A61B 17/34* (2006.01)

(52) U.S. Cl.
CPC .......... *A61B 8/4422* (2013.01); *A61B 8/0841* (2013.01); *A61B 8/4236* (2013.01); *A61B 90/40* (2016.02); *A61B 2017/3413* (2013.01)

(58) Field of Classification Search
CPC ......... A61B 46/00; A61B 46/10; A61B 46/20; A61B 46/40; A61B 2046/205; A61B 2050/002; A61B 8/4236; A61B 8/4422; A61B 90/40; A61B 8/0841; A61B 2017/3413; A61B 46/23
See application file for complete search history.

(56) References Cited

U.S. PATENT DOCUMENTS

| 481,735 | A | * | 8/1892 | Pidgin | B42D 1/08 24/DIG. 11 |
|---|---|---|---|---|---|
| 1,524,399 | A | * | 1/1925 | Krueger | B65D 5/46008 16/407 |
| 4,119,268 | A | * | 10/1978 | Segura | B65D 75/56 383/21 |
| 4,650,705 | A | * | 3/1987 | Ghodsian | A61B 17/0281 428/40.6 |
| 4,829,995 | A |   | 5/1989 | Metters |   |
| 5,230,119 | A | * | 7/1993 | Woods | A45D 40/26 128/917 |

(Continued)

*Primary Examiner* — Long V Le
*Assistant Examiner* — Angela M Hoffa
(74) *Attorney, Agent, or Firm* — Dority & Manning, P.A.

(57) ABSTRACT

In one aspect, the present subject matter is directed to a barrier device. The barrier device has a generally flat base with a width and a length. The base has a top portion and an opposite bottom portion. A surface of the bottom portion includes adhesive. A barrier extends upwardly from the base, the barrier having a generally flat first side and an opposite generally flat second side. A width between the first side of the barrier and the second side of the barrier is less than the width of the base.

8 Claims, 2 Drawing Sheets

(56) References Cited

U.S. PATENT DOCUMENTS

| | | | | |
|---|---|---|---|---|
| 5,419,009 | A * | 5/1995 | Assis | B65D 5/46016 16/407 |
| 5,771,524 | A * | 6/1998 | Woods | A45D 40/00 15/209.1 |
| 5,876,081 | A * | 3/1999 | Melody | B65D 5/46032 229/117.26 |
| 6,044,515 | A * | 4/2000 | Zygmont | B05C 17/00 15/209.1 |
| 6,464,815 | B1 * | 10/2002 | Beaudry | A45D 29/11 15/208 |
| 6,493,898 | B1 * | 12/2002 | Woods | B05C 17/00 15/209.1 |
| 7,036,513 | B2 | 5/2006 | Wallin | |
| 8,434,803 | B1 * | 5/2013 | An | B25J 1/04 294/212 |
| 2003/0057247 | A1 * | 3/2003 | Farr | B60J 10/45 225/93 |
| 2008/0015442 | A1 * | 1/2008 | Watson | A61B 8/0841 600/459 |
| 2010/0041990 | A1 * | 2/2010 | Schlitt | A61B 17/3403 600/439 |
| 2016/0015891 | A1 * | 1/2016 | Papiorek | A61M 5/158 604/180 |
| 2017/0086782 | A1 * | 3/2017 | Hagy | A61B 8/0841 |

* cited by examiner

ULTRASOUND BARRIER DEVICES AND METHODS RELATED THERETO

CROSS-REFERENCE TO RELATED APPLICATION

The present application is based on and claims priority to U.S. Provisional Application 61/726,929 having a filing date of Nov. 15, 2012, which is incorporated by reference herein.

BACKGROUND

In medicine, ultrasound has become one of the most utilized imaging methods. Ultrasound applications employ a transducer that generates and sends ultrasound waves into a patient. Ultrasound can be used to guide needles and catheters to a site under the skin for biopsies and insertion into blood vessels. These ultrasound guided techniques have dramatically increased the accuracy of hitting the target blood vessel or tissue while decreasing the number of complications of such procedures performed without ultrasound. However, since an ultrasound probe is not sterile, there exists a risk of introducing infection if the probe crosses into the area where the needle or catheter punctures the skin.

To decrease the likelihood of infection from the probe, sterile ultrasound kits are typically used that include a sterile cover for the probe, sterile ultrasound gel that is needed as a contact with the skin surface to use the probe, and/or sterile drapes. These kits add significant cost to the procedure, take time to prepare and use, and generally require two individuals to use—the person performing the procedure and an assistant.

As such, it would be desirable to provide a device that provides a sterile barrier between a puncture site and an ultrasound probe site without the aforementioned limitations. Methods relating to such a device would also be desirable.

SUMMARY

Aspects and advantages of the invention will be set forth in part in the following description, or may be obvious from the description, or may be learned through practice of the invention.

In one aspect, the present subject matter is directed to a barrier device. The barrier device has a generally flat base with a width and a length. The base has a top portion and an opposite bottom portion. A surface of the bottom portion includes adhesive. A barrier extends upwardly from the base, the barrier having a generally flat first side and an opposite generally flat second side. A width between the first side of the barrier and the second side of the barrier is less than the width of the base.

In yet another aspect of the present disclosure, a method for utilizing a barrier device with an ultrasound guided procedure is described. The method includes positioning a barrier device on a patient. The method further includes positioning an ultrasound probe adjacent to the second side of the barrier and positioning a needle adjacent to the first side of the barrier, wherein the barrier separates the ultrasound probe and the needle.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
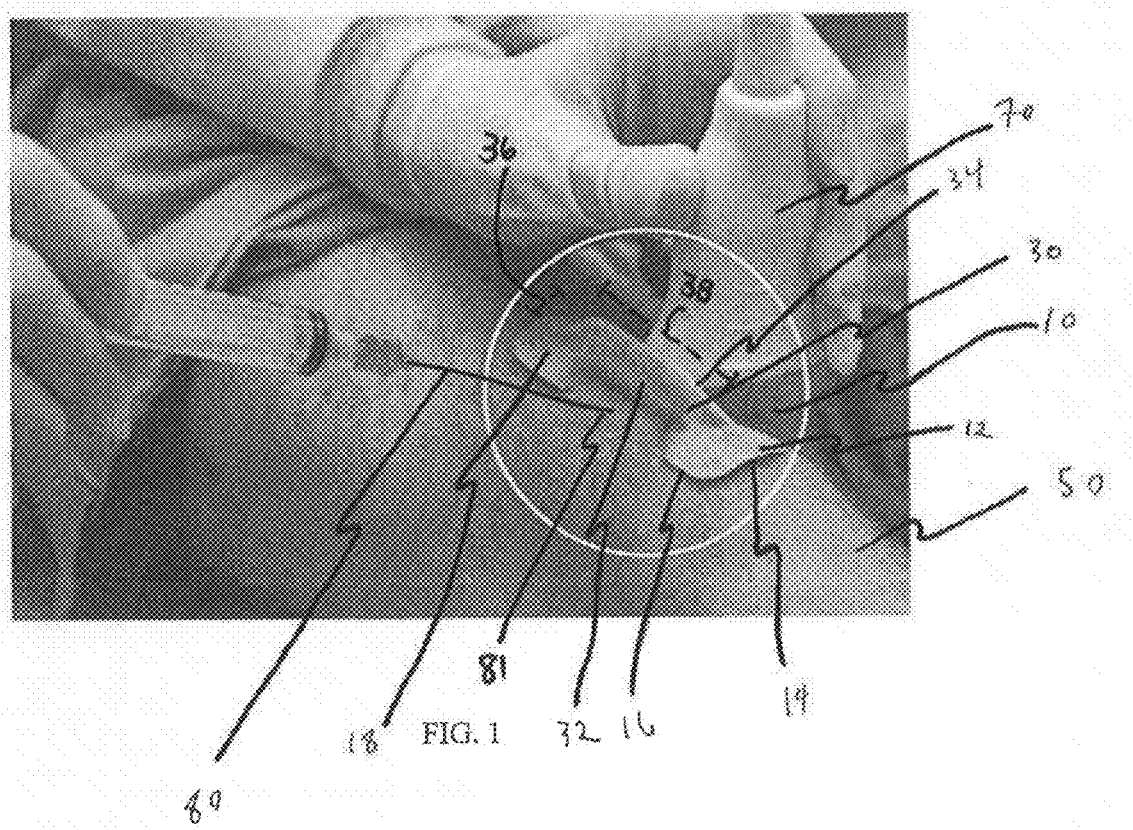
FIG. 1 depicts a perspective view of a device in accordance with certain exemplary embodiments of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

The present disclosure is generally directed to a barrier device for use with ultrasound guided procedures. The barrier device of the present disclosure can be adhered to a patient so that an ultrasound probe is utilized on one side of the barrier device and a needle or other instrument is positioned on the other side of the ultrasound device. In particular, the devices described herein prevent a non-sterile ultrasound probe and/or ultrasound gel from moving to a sterile surface near an injection site. The devices of the present disclosure can be utilized to create a wall to prevent contamination of a puncture site to reduce infection risk.

Advantageously, the present disclosure allows for ultrasound guided procedures to be completed more quickly and without requiring an assistant as is typically needed. The barrier devices described herein are also more cost effective than pre-packaged ultrasound sterility kits.

Referring to FIG. 1, a barrier device 10 in accordance with the present disclosure is illustrated. The device 10 is positioned on a patient's knee 50. However, the device 10 of the present disclosure can be positioned at any suitable location to provide a barrier between an ultrasound probe and an instrument, such as a needle.

The device 10 includes a base 12 having a width 14 and length 16. Measurements for length and width can vary depending on the location that device 10 is to be positioned but length can generally be from about 10 mm to about 100 mm and a width can generally be from about 1 mm to about 50 mm. In certain aspects of the present disclosure, the width of the base can narrow (as is illustrated) to a second width such that the width is similar to that of barrier 30 (as will be described in greater detail herein). Base 12 also includes a top portion 18 and bottom portion 20 (shown in FIG. 2).

Figure 2:
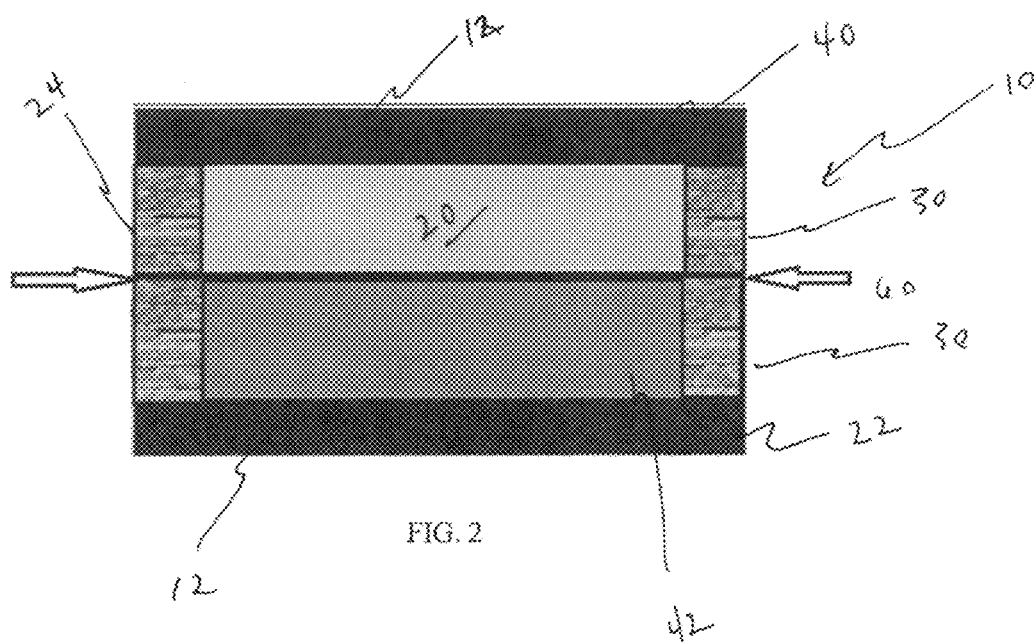
FIG. 2 depicts and expanded view of a device in accordance with certain exemplary embodiments of the present disclosure.

FIG. 2 illustrates an expanded view of device 10 in accordance with certain aspects of the present disclosure. Device 10 can be formed by folding a generally rectangular shaped material 40 along fold 60 so as to create base 12 and barrier 30. Bottom portion 20 of base 12 includes adhesive 22 to adhere device 10 to patient. Any suitable adhesive can be utilized. For example, a silk tape, such as Durapore® Tape available from 3M Company, or any type of similar adhesive tape suitable for medical use can be utilized that does or does not include a protective strip covering the adhesive. Adhesive 22 can be located around one or more of top, bottom, and/or sides of the perimeter 24 of base 12.

Turning back to FIG. 1, barrier 30 extends upwardly from base 12. Barrier 30 is designed to separate ultrasound probe 70 from instrument insertion site 81. In this regard, barrier can be formed of a substantially rigid material so that barrier remains upright when device is placed on patient. Referring to FIG. 2, in certain aspects of the present disclosure, one or more additional elements, such as insert 42 can be utilized to provide sufficient rigidity to barrier 30. For instance, as shown, when generally rectangular shaped material 40 is folder over itself, insert 42 can be placed on one side of fold line 60 and sandwiched by material 40 so as to reinforce the portion of material 40 that becomes barrier 30. Insert can be any suitable material, such as plastic or the like. Insert can be of any suitable length, width, and thickness. For example, in certain aspects of the present disclosure, insert can have a length of from about 10 mm to about 95 mm, a width of from about 1 mm to about 5 mm, and a thickness of from about 0.5 mm to about 2 mm. In addition, any other suitable rigidity enhancing element as would be understood by one of ordinary skill in the art can be utilized as well.

With reference again to FIG. 1, barrier 30 can include a first side 32 and an opposite second side 34. The barrier has a width 36 and length 38. For instance, in certain aspects of the present disclosure, the width 36 can be measured between first side 32 and second side 34. Such width can be less than width 14 of base 12. Measurements for length and width can vary depending on the location that device is to be positioned but length can generally be from about 10 mm to about 100 mm and width can be from about 1 mm to about 10 mm. Barrier 30 can be generally perpendicular to base 12.

While illustrated as being generally flat, barrier can have a curved shape or any other suitable to accommodate a curved portion of the body. Similarly, depending on the application, base can be curved or have any other suitable shape to allow base to adhere flush to patient. For instance, in certain aspects of the present disclosure, both base and barrier can be rounded to accommodate positioning on a joint of a patient.

The device 10 can be constructed of one or more materials of suitable strength that are acceptable for medical applications. Base 12 and barrier 30 can be formed from the same material or from different materials. In certain aspects, as described above, base 12 and barrier 30 are formed from folding a single piece of material. The material can be flexible, latex-free, and antimicrobial. The material should be sufficient to be impervious to blood or other body fluids. Suitable materials can include woven fabrics, polymers, or the like, namely polyolefin film, polyurethane polymer, polyethylene, polyethylene vinyl acetate, polyurethane foam, and can also be made from a textile, non-woven material, rubber, and the like. As described previously, adhesive can be affixed to one portion of the device or material can simply include adhesive attributes, such adhesive being similarly suitable for medical applications.

Device can be configured to be folded and packaged so as to be easily shipped and sold. For instance, similar to a conventional bandage, barrier device can include a disposable package and that incorporates one or more protective strips as a part thereof over adhesive portions. For instance, in certain aspects of the present disclosure, bottom portion of base can include a protective strip while barrier can be folded over bottom portion so that the entire device can be packaged as a generally flat device. Upon unwrapping device from packaging, barrier can be folded upright and device can be placed on patient. In this manner, device can be remain sterile and easy to package prior to use.

In use, a health care worker can clean the area on patient at which an ultrasound guided procedure is to take place using conventional sterilizing methods. The worker can then remove a protective strip (not shown) covering the adhesive layer and place the device 10 on patient, such as illustrated patient knee 50. Ultrasound gel (not shown) can be applied on and around the location of intended ultrasound on one side of device 10. Ultrasound probe 70 can be positioned adjacent to one side of device 10 and instrument 80, such as the illustrated needle, can be inserted into patient with guidance from ultrasound probe 70 on other side of device 10. In this manner, the disclosed barrier device of the present disclosure can create a wall of protection from contamination of the area on the skin to be punctured by a needle or catheter in ultrasound guided procedures. The barrier device separates the area where the non-sterile ultrasound probe is used in identifying the target site below the skin and the area that is sterilized before puncture, decreasing the risk of infection to the patient. Using the barrier device reduces the time, cost, and additional personnel presently necessary to perform ultrasound guided procedures using a standard ultrasound kit. The barrier device of the present disclosure can be an effective, efficient, and cost effective alternative to the present methods of performing ultrasound guided procedures since ultrasound guided procedures are rapidly increasing in numbers across many areas of medicine.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for utilizing a barrier device with an ultrasound guided procedure, the method comprising:
positioning a barrier device on a patient, the barrier device comprising a generally flat base with a width and a length, the base comprising a top portion and an opposite bottom portion, a surface of the bottom portion comprising adhesive that adheres the base to the patient, the barrier device further comprising a barrier extending upwardly from the base, the barrier having a generally flat first side and an opposite generally flat second side, a width between the first side of the barrier and the second side of the barrier being less than the width of the base, further wherein the base has a second width, the second width being generally equal to the width between the first side of the barrier and the second side of the barrier;
positioning an ultrasound probe adjacent to the second side of the barrier;
positioning an instrument adjacent to the first side of the barrier, wherein the barrier separates the ultrasound probe and the instrument; and guiding the positioned instrument to a target site within the patient using ultrasound images obtained by the positioned ultrasound probe.

2. The method of claim 1, wherein the barrier is substantially rigid.

3. The method of claim 1, wherein the base and the barrier comprise the same material.

4. The method of claim 3, wherein the instrument is a needle.

5. The method of claim 3, wherein the material is antimicrobial.

6. The method of claim 1, wherein the barrier is generally perpendicular to the base.

7. The method of claim 1, further comprising a rigid element sandwiched between the first side of the barrier and the second side of the barrier.

8. The method of claim 7, wherein the rigid element comprises plastic.

* * * * *